United States Patent
Friesz et al.

(10) Patent No.: US 9,193,703 B2
(45) Date of Patent: Nov. 24, 2015

(54) PROCESS FOR PREPARATION OF DRONEDARONE BY MESYLATION

(75) Inventors: Antal Friesz, Budapest (HU); Csaba Huszar, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/007,431

(22) PCT Filed: Mar. 27, 2012

(86) PCT No.: PCT/HU2012/000019
§ 371 (c)(1),
(2), (4) Date: Dec. 4, 2013

(87) PCT Pub. No.: WO2012/131408
PCT Pub. Date: Oct. 4, 2012

(65) Prior Publication Data
US 2014/0081035 A1    Mar. 20, 2014

(30) Foreign Application Priority Data
Mar. 29, 2011 (HU) .................................. 1100167

(51) Int. Cl.
*C07D 307/81* (2006.01)
(52) U.S. Cl.
CPC .................... *C07D 307/81* (2013.01)
(58) Field of Classification Search
CPC .................................................. C07D 307/81
USPC ....................................................... 549/468
See application file for complete search history.

(56) References Cited

U.S. PATENT DOCUMENTS

| | | |
|---|---|---|
| 3,577,441 A | 5/1971 | Kaminsky et al. |
| 3,657,350 A | 4/1972 | Mooradian et al. |
| 3,937,737 A | 2/1976 | Eiglmeier |
| 4,243,405 A | 1/1981 | Balasubramanyan et al. |
| 4,666,931 A | 5/1987 | Ohishi et al. |
| 5,066,803 A | 11/1991 | D'Ambra et al. |
| 5,223,510 A | 6/1993 | Gubin et al. |
| 6,555,697 B1 | 4/2003 | Schlama |
| 6,828,448 B2 | 12/2004 | Fino et al. |
| 6,846,936 B2 | 1/2005 | Biard |
| 6,855,842 B1 | 2/2005 | Schlama et al. |
| 6,949,583 B2 | 9/2005 | Assens et al. |
| 6,984,741 B2 | 1/2006 | Magerlein |
| 7,148,240 B2 | 12/2006 | Assens et al. |
| 7,312,345 B2 | 12/2007 | Gutman et al. |
| 7,517,876 B2 | 4/2009 | Klein et al. |
| 8,143,269 B2 | 3/2012 | Whitten et al. |
| 8,501,971 B2 | 8/2013 | Friesz et al. |
| 8,658,808 B2 | 2/2014 | Kretzschmar et al. |
| 8,658,809 B2 | 2/2014 | Friesz et al. |
| 8,674,121 B2 | 3/2014 | Kretzschmar et al. |
| 8,686,180 B2 | 4/2014 | Bon et al. |
| 8,748,636 B2 | 6/2014 | Bailly et al. |
| 8,796,489 B2 | 8/2014 | Bailly et al. |
| 8,816,103 B2 | 8/2014 | Friesz et al. |
| 8,871,956 B2 | 10/2014 | Bailly et al. |

(Continued)

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

Thornber, C. W. "Isosterism and molecular modification in drug design." Chem. Soc. Rev. 8.4 (1979): 563-580.*
Johnson Matthey Handbook of Pharmaceutical Catalysis, 2009.*
International Search Report dated Jun. 5, 2012 issued in PCT/HU2012/000019.
Abramenko, et al., Polymethine Dyes—Furo[2,3-g] Benzothiazole Derivatives, Chemistry of Heterocyclic Compounds, vol. 11, (1975), pp. 1361-1364.
Adams, R. et al. Quinone imides. IV. P-Quinone monosulfonimides. Journal of the American Chemical Society. 1951, vol. 73, pp. 1145-1149.

(Continued)

*Primary Examiner* — Samantha Shterengarts
*Assistant Examiner* — Matt Mauro
(74) *Attorney, Agent, or Firm* — Morrison & Foerster LLP

(57) ABSTRACT

The invention relates to a novel process for preparation of N-[2-n-butyl-3-[4-[3-(di-n-butylamino)-propoxy]-benzoyl]-benzofuran-5-yl]methanesulfonamide (I) and pharmaceutical acceptable salts thereof, where a salt of (5-amino-2-butyl-1-benzofuran-3-yl){4-[3-(di-n-butylamino)propoxy]phenyl}methanone of formula (II)—where A is a mono- or dibasic acid forming an acid addition salt with the compound of formula (II), n is 1 if A is dibasic acid and n is 1 or 2 if A is a monobasic acid—is reacted with a mesylating reagent in a heterogen reaction, if desired, in the presence of a phase transfer catalyst. The invention also relates to the novel salts of compound of formula (II), for the preparation thereof and their use in the preparation of dronedarone.

(I)

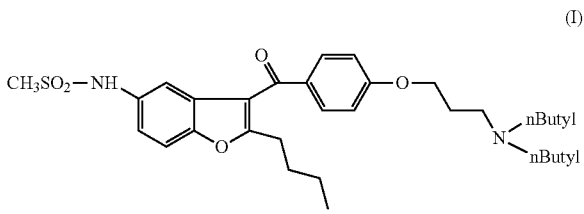

(II)

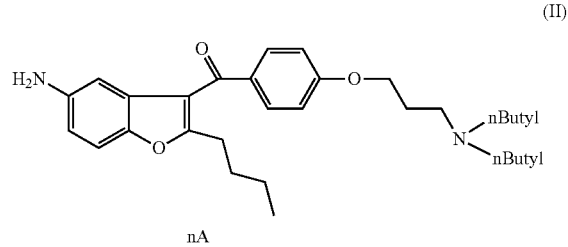

14 Claims, No Drawings

(56) References Cited

U.S. PATENT DOCUMENTS

| | | |
|---|---|---|
| 8,884,033 B2 | 11/2014 | Bon et al. |
| 8,889,734 B2 | 11/2014 | Friesz et al. |
| 8,962,869 B2 | 2/2015 | Grimaud et al. |
| 9,024,046 B2 | 5/2015 | Friesz et al. |
| 2008/0033209 A1 | 2/2008 | Szarvas et al. |
| 2010/0087415 A1 | 4/2010 | Whitten et al. |
| 2010/0273764 A1 | 10/2010 | Andrews et al. |
| 2013/0023678 A1 | 1/2013 | Priem et al. |
| 2013/0109868 A1 | 5/2013 | Friesz |
| 2013/0289287 A1* | 10/2013 | Vishnu Newadkar et al. ............... 549/468 |
| 2014/0018553 A1 | 1/2014 | Grimaud et al. |
| 2014/0114081 A1 | 4/2014 | Friesz et al. |
| 2015/0005515 A1 | 1/2015 | Friesz et al. |
| 2015/0018568 A1 | 1/2015 | Friesz |
| 2015/0031901 A1 | 1/2015 | Bon et al. |
| 2015/0031902 A1 | 1/2015 | Huszar et al. |

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO 02/48078 * | 6/2002 |
| WO | WO 02/48078 A1 | 6/2002 |
| WO | WO 02/48132 A1 | 6/2002 |
| WO | WO 0248132 A1 * | 6/2002 |
| WO | WO 03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO 2009044143 A2 * | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO 2012/004658 A2 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO 2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz, Lilian et al., "Novel N-Aryl and N-Heteroaryl Sulfamide Synthesis via Palladium Cross Coupling," Organic Letters (2004), vol. 6, No. 16, pp. 2705-2708.

Ando, M.E. et al. (1982). "Motion at the Active Site of Tosylchymotrypsin," *Journal of the American Chemical Society* 104(1 1):3172-3178.

Anjanappa, Prakash et al., "2-(Trimethylsilyl)ethanesulfonyl amide as a new ammonia equivalent for palladium—catalyzed amination of aryl halides," Tetrahedron Letters (2008), vol. 49, pp. 4585-4587.

Bartoli, G. et al. (1991). "Unexpected Elimination to α,β-Alkynylketones in the Reaction of Dianions of 1-Arylenaminones with Trimethylchlorosilane," Tetrahedron Letters 32(48):7091-7092.

Batra, S. et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli, Shanthaveerappa K. et al., "Application of Ionic Liquid Halide Nucleophilicity for the Cleavage of Ethers: A Green Protocol for the Regeneration of Phenols from Ethers," Journal of Organic Chemistry (2004), vol. 69, pp. 3340-3344.

Bourgery, et al., Synthesis and Antiarrhythmic Activity of New Benzofuran Derivatives, Journal of Medicinal Chemistry, (1981), vol. 24, No. 2, pp. 159-167.

Burton, George et al., "Palladium-Catalyzed Intermolecular Coupling of Aryl Chlorides and Sulfonamides under Microwave Irradiation," Organic Letters (2003), vol. 5, No. 23, pp. 4373-4376.

Castellino, Angelo J. et al., "Synthesis of Benzofurans from Oxygenated Phenoxyamines," Journal of Organic Chemistry (1984), vol. 49, pp. 4399-4404.

Chauhan, Shive M.S. et al., "Microwave assisted dealkylation of alkyl aryl ethers in ionic liquids," Journal of Chemical Research (2004), p. 693-694.

Cheng, Lili et al., "Facile Cleavage of Ethers in Ionic Liquid," Bulletin of the Chemical Society of Japan (2007), vol. 80, No. 10, pp. 2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," *Current Topics in Catalysis* 6:19-33.

Denmark, S.E. et al. (2008). "Lewis base catalysis in organic synthesis," *Angew. Chem. Int. Ed.* 47(9):1560-1638.

Douglass, I.B. (1959). "Some New Reactions of Methanesulfenyl Chloride," *Journal of Organic Chemistry* 24:2004-2006.

Fehnel, EA. (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

Gilow, H.M. et al. (Jun.-Jul. 1991). "Sulfenylation of Some Pyrroles and Indoles," *J. Het. Chem.* 28:1025-1034.

Groves, J.K. (1972). "The Friedel—Crafts Acylation of Alkenes," Chem. Soc. Rev. 1:73-97.

Gutowski, Keith E. et al., "Prediction of the Formation and Stabilities of Energetic Salts and Ionic Liquids Based on ab Initio Electronic Structure Calculations," The Journal of Physical Chemistry B (2005), vol. 109, pp. 23196-23208.

Haddadin et al. (1976). "Reaction to Benzofurazan Oxide with Unsymmetrical 1, 3-Diketones: Steric Polar Effects," *Tetrahedron* 32:719-724.

Hauser, CR. et al. (1948) "Alkaline cleavage of unsymmetrical β-diketones. Ring opening of acylcyclohexanones to form ε-acylcaproic acids," Journal of the American Chemical Society. 70:4023-4026.

(56) References Cited

OTHER PUBLICATIONS

Headley, Lindsay Sanders et al., "Dynamic Solvation in Imidazolium-Based Ionic Liquids on Short Time Scales," Journal of Physical Chemistry (2006), vol. 110, pp. 9549-9554.
Horton et al. (1967). "Reactions With Reactive Alkyl Halides," *J. Meth. In Enzymology* 11:556-565.
Ikawa, Takashi et al., "Pd-Catalyzed Amidations of Aryl Chlorides Using Monodentate Biaryl Phosphine Ligands: A Kinetic, Computational, and Synthetic Investigation," Journal of the American Chemical Society (2007), vol. 129, pp. 13001-13007.
Imori et al. (2006). "Efficient Demethylation of N,N-Dimethylanilines with Phenyl Chloroformate in Ionic Liquids," *Synlett*. 16:2629-2632.
Joshi, KC. et al. (1986). "Some New Fluorinated β-Ketoamines and Their Copper Complexes," Synth. React. Inorg. Met.—Org. Chem. 1986, vol. 16(7):1009-1024.
Krongauz, ES. et al. Poly(anilophenylquinoxaline)s. Inst. Elementoorg. Soedin. 1986, vol. 28(4), p. 771 (Abstract).
Kurti, L. et al. Strategic Applications of Named Reactions in Organic Synthesis. El Sevior. 2005, pp. 448-449.
Kwiatkowski, E. et al. (1978). Metal Benzoylpivaloylmethanates, Part I. Free Ligands and Copper(II) Chelates. Transition Met. Chem. 3:305-308.
Laszlo, Pierre et al., "Catalysis of Friedel-Crafts Alkylation by a Montmorillonite Doped with Transition-Metal Cations," Helvetica Chimica Acta (1987), vol. 70, pp. 577-586.
Liu, Tao et al., "Cleavage of Methyl Ethers of Flavones by Chloroaluminate Ionic Liquid," Synthetic Communications (2004), vol. 34, pp. 3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofeni1)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March, J. (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.
March, J. (Jul. 1, 1992). "Aliphatic Nucleophilic Substitution," Part 2 in *Advanced Organic Chemistry, Reactions, Mechanism and Structure*, 4th edition, Wiley Interscience, pp. 442.
Marvel, C.S. et al. (1941). "Diphenylacetic Acid," *Org. Synth. Coll.* vol. 1, 224-225.
Mehrotra, PK. et al. (2001). Search for new chemical entities as menses inducing agents. Contraception. 64:187-191.
Munch, R. et al. (1946). "The Preparation of Some α-Dialkylamino-ω-Methylaminoalkanes," *J. Am. Chem. Soc.* 68:1297-1299.
Nagy et al. (2007). "Isomorphous Substitution in Zeolites," *Mol. Sieves* 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.
Pal et al., "Synthesis of monohydroxy-functionalized triphenylene discotics: green chemistry approach," Tetrahedron (2007), vol. 63, pp. 6874-6878.
Roshchin, et al., Synthesis of Benzofurans via Pd2+-Catalyzed Oxidative Cyclization of 2-Allylphenols, Journal of Organometallic Chemistry. vol. 560, No. 1-2. (1998), pp. 163-167.
Sanfilippo, P.J. (1988). "Synthesis of (aryloxy)alkylamines. 1. Novel antisecretory agents with H+K+-ATPase inhibitory activity," *J. Med. Chem.* 31(9):1778-1785.
Serajuddin, ATM. Salt formation to improve drug solubility. Advanced Drug Delivery Reviews 2007, vol. 59, pp. 603-616.

Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry, vol. 208, pp. 234-237.
Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Ślusarska, E. et al. (Feb. 1981). "One-Pot Phase-Transfer-Catalysed N-Alkylation of Diphenylphosphinamide with Alcohols in the Presence of Methanesulfonyl Chloride," *Synthesis* 155-156.
Son, J-K. et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.
Sun, Lo. et al. N-{2-[2-( 4-Phenylbutyl)benzofuran-4-yl]cyclopropylmethyl}-acetamide: an orally bioavailable melatonin receptor agonist. Bioorganic & Medicinal Chemistry Letters. 2004, vol. 14, pp. 5157-5160.
Tanaka, M. (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Upthagrove, A.L. et al. (Nov. 2001). "Importance of Amine p$K^a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser, CC. et al. (1989). "Kinetics and Mechanisms for the Two-phase Reaction between Aqueous Aniline and Benzoyl Chloride in Chloroform, with and without Pyridine Catalysis," *J. Org. Chem.* 54:150-154.
Weissman, Steven A. et al., "Recent advances in ether dealkylation," Tetrahedron (2005), vol. 61, pp. 7833-7863.
Weitkamp et al. (1986). "Isomorphe Substitution in Zeolithen: Katalyse an Boro-, Alumo-und Galio-Silicaten mit ZSM-5-Strukter," *Chem. Ing. Tech.* 58(12):969-971 (with English Translation).
Wikipedia. (Nov. 5, 2012). "Reduction of Nitro Compounds.".
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts, G.M., Greene's Protective Groups in Organic Synthesis, Fourth Edition, 2006, John Wiley and Sons, Chapter 7, Protection for the Amino Group, pp. 696-926.
Yang, H. et al. (2009). "Structure-based virtual screening for identification of novel 11 β-HSD1 inhibitors," European J. of Medicinal Chem. 44(3):1167-1171.
Yin, Jingjun et al., "Palladium-Catalyzed Intermolecular Coupling of Aryl Halides and Amides," Organic Letters (2000), vol. 2, No. 8, pp. 1101-1104.
Yin, Jingjun et al., "Pd-Catalyzed Intermolecular Amidation of Aryl Halides: The Discovery that Xantphos Can Be Trans-Chelating in a Palladium Complex," Journal of the American Chemical Society (2002), vol. 124, pp. 6043-6048.
Zasshi, Y. (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al. (Copy not attached).
U.S. Appl. No. 14/403,528, filed Nov. 24, 2014, by Huszar et al. (Copy not attached).

* cited by examiner

PROCESS FOR PREPARATION OF DRONEDARONE BY MESYLATION

FIELD OF THE INVENTION

This invention relates to a novel process for the preparation of dronedarone and pharmaceutically acceptable salts thereof, to novel intermediary compounds used in this process and their preparation.

TECHNICAL BACKGROUND

Dronedarone is a known drug for the treatment of arrhythmia and has the chemical name of N-[2-n-butyl-3-[4-[3-(di-n-butylamino)propoxy]benzoyl]benzofuran-5-yl]methanesulfonamide [see also formula (I) below]. There are some known processes for the preparation of dronedarone as follows:

In EP 0471609 the following scheme is disclosed for the preparation of dronedarone [Process A]

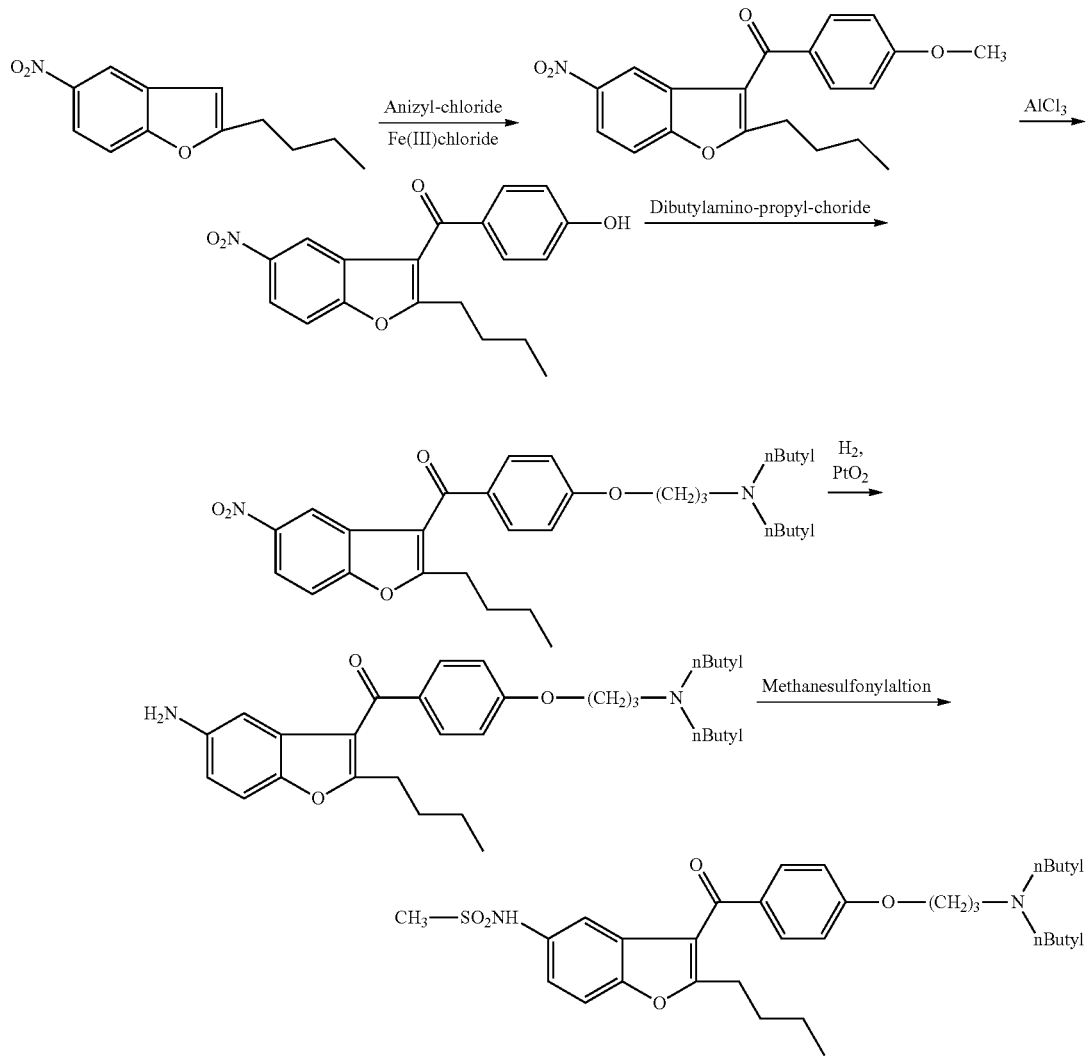

The above mentioned patent description discloses some new intermediary compounds, too.

In WO 02/48078 the following scheme is disclosed for the preparation of dronedarone [Process B]:

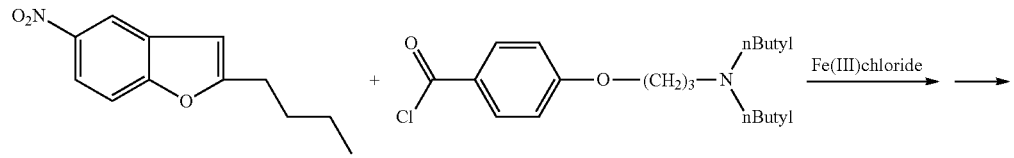

-continued

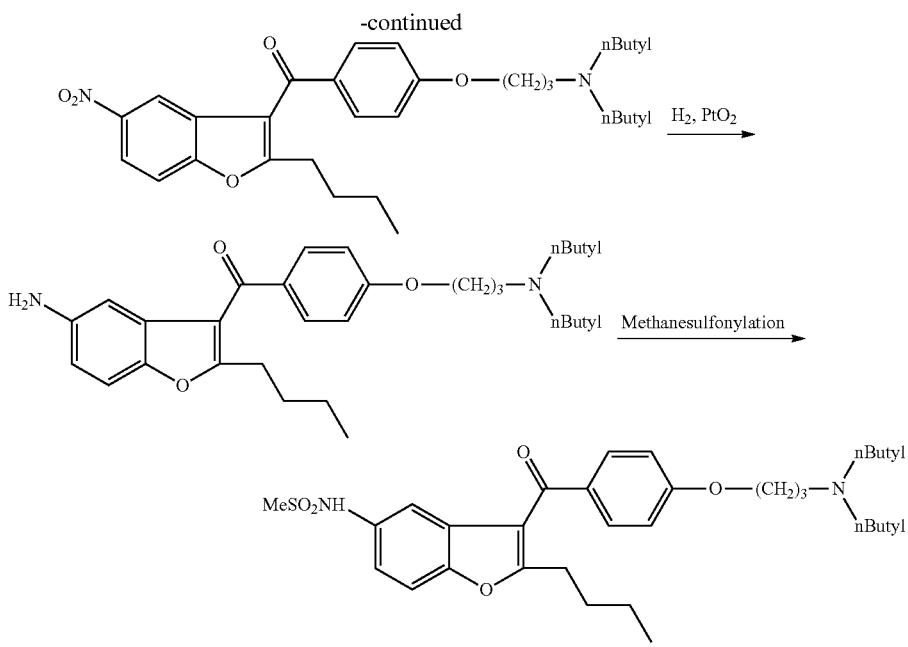

The novelty of the process is based on the adaptation of the Friedel-Crafts reaction in the first step. The process and the intermediary compounds used for the preparation of the benzoylchloride compound of the first step are also disclosed in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so called superconvergent route. In the first step of it 5-amino-2-butyl-benzofuran

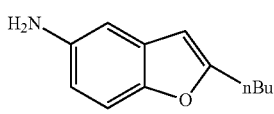

is mesylated and the obtained 2-butyl-5-methanesulfonamido-benzofuran (in HCl salt form) is further reacted in the next step as follows:

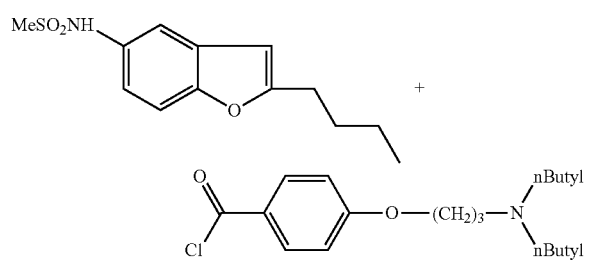

In this process the order of reaction steps are altered, the reduction and the methansulfonylation steps are performed at the beginning of the procedure. Besides the reaction route for preparation of dronedarone, the starting material 2-butyl-5-methansulfonamido-benzofuran and its preparation is also claimed.

From among the mentioned procedures the first one [Process A] is the so called linear synthesis. In this way of procedure the different parts of the dronedarone are stepwise built up on the starting compound. This method is the least economical because the step by step building of the chemical groups is performed where more and more complicated and expensive molecules are applied which rises the costs of preparation. Furthermore, it comprises complicated and dangerous reaction step because aluminium chloride is used in the cleaving reaction of the methoxy group which makes the industrial feasibility more complicated.

In WO 02/48078 (Process B) a shorter synthetic route is disclosed which makes this process more economical, but its last reaction step remained the methansulfonylation reaction of the amino group. This reaction step (see the method described in example 6 of of WO 02/48078) is complicated and give a low yield, only 61.6%. Pure product can be obtained after purification using chromatographic column purification, which method is necessary because of the separation difficulties of the bis-methanesulfonylated product.

The process disclosed in WO 02/48132 (process C) is simpler and more economical taken into consideration the number of the reaction steps. Unfortunately, in the last reaction step rather impure dronedarone.HCl (hydrochloride) is formed which is the obvious consequence of the presence of dibutylamino group in the Friedel-Crafts reaction. According to Examples 3 and 4, the crude dronedarone hydrochloride is prepared with a yield of 90% which is further purified and finally the crude dronedarone base is produced with a yield of 86%. This base is reacted with hydrogen chloride gas dissolved in isopropanol which results in pure dronedarone hydrochloride salt. No yield is given for this reaction step. According to example 5 crude dronedarone hydrochloride salt is prepared with a yield of 90%, which is washed with water and reacted with hydrogen chloride gas dissolved in isopropanol, resulting dronedarone hydrochloride salt again. The quality of this product is not known. However, neither the components used in the Friedel-Crafts reaction nor the resulted products and by-products are soluble in water, the washing step with water cannot result any purification apart from the removal of inorganic salts.

There is another drawback of this process, namely, a dimesylated side-product is formed in the mesylation reaction of the 5-amino-2-butyl-benzofuran. The purification is carried out by crystallization which has a yield of 78.5%.

It is known from example 3 of EP 0 471 609 (Process A) that the methanesulfonylation reaction of amino group in preparation of dronedarone is performed in dichloromethane solvent in presence of triethylamine as acid binding agent and using methanesulfonyl chloride as methanesulfonylating reagent. The reaction is performed at room temperature, probably, since the applied temperature is not given. The reaction time is 20 hours. The yield of crude dronedarone is 100% but pure dronedarone can be prepared from the crude material only with a yield of 61.6%. In another example the purification of crude dronedarone is made by hexane. The yield of this purification step is 56.5%. The purity of the obtained pure dronedarone is 96.1% (HPLC).

In example 35 of EP 0 471 609 (Process A) the methanesulfonylation reaction of 2-n-butyl-5-amino-benzofurane is disclosed. The solvent is carbon tetrachloride and trietylamine is applied as base and methanesulfonyl chloride is used as methanesulfonylating reagent in an amount of 3 equivalents. After 6 hours reaction time the 2-(bis-methanesulfonamido)-2-n-butyl-benzofurane[3] is separated.

It is quite obvious from these two experiments that the selective mono-methanesulfonylation of the amino group is difficult and, according to example 3 mentioned before, beside the unreacted amino compound bis-methanesulfonylated compound (2) is also present. This is the reason of the moderate yield of the purification of crude dronedarone and of the relatively low purity level of 96.1% (HPLC) (which disables the direct use of the obtained material for pharmaceutical purpose).

It is an object of present invention to provide a novel process for the preparation of dronedarone of formula (I), starting with known and commercially available materials, applying simple and environmentally compatible reagents and solvents to afford high overall yields and good purity of the product.

SUMMARY OF THE INVENTION

The main aspect of the invention is a novel process for preparation of N-[2-n-butyl-3-[4-[3-(di-n-butylamino)-propoxy]-benzoyl]-benzofuran-5-yl]methanesulfonamide (dronedarone) (I)

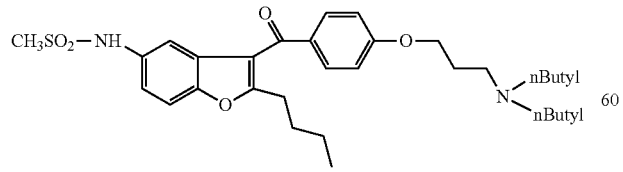

(I)

and pharmaceutical acceptable salts thereof, in which a salt of (5-amino-2-butyl-1-benzofuran-3-yl){4-[3-(di-n-butylamino)propoxy]phenyl}methanone of formula (II)

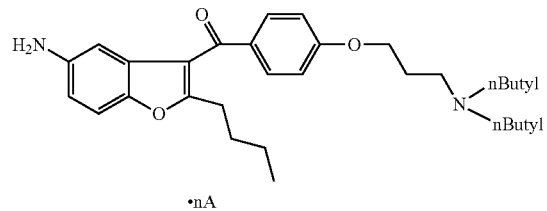

(II)

where
A is a mono- or dibasic acid forming an acid addition salt with the compound of formula (II), and
   n is 1 if A is dibasic acid, and
   n is 1 or 2 if A is a monobasic acid,
   is reacted with a mesylating reagent in a heterogeneous reaction if desired, in the presence of a phase transfer catalyst.

The obtained salt is separated, if desired, the free base form is delibareted from it and, if desired, the obtained free compound is transformed into another salt.

The applicable acid for the preparation of pharmaceutically acceptable salts can be any inorganic or organic acid which forms an acid addition salt with the compound of general formula (I). Exemplary acids which can form an acid addition salt are as follows: acetic acid, adipic acid, alginic acid, ascorbic acid, aspartic acid, benzoic acid, benzenesulfonic acid, methansulfonic acid, ethansulfonic acid, boric acid, butyric acid, citric acid, fumaric acid, hydrogen chloride, hydrogen bromide, hydrogen iodide, 2-hydroxyethanesulfonic acid, maleic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the amide part of the mesylate group of the compound of general formula (I) (see the "left side" of the molecules) a salt formation can be carried out by a strong base, e.g. an alkaline hydroxide, typically by sodium hydroxide. However, these salts have less practical importance, but they are within the scope of salts which can be prepared by the claimed process, i.e. the phrase "salts" embraces both the acid addition salts and the salts formed by bases (basic salts).

Another aspect of the invention relates to the novel intermediary salts of (5-amino-2-butyl-1-benzofuran-3-yl){4-[3-(di-n-butylamino)propoxy]-phenyl}methanone of formula (II)

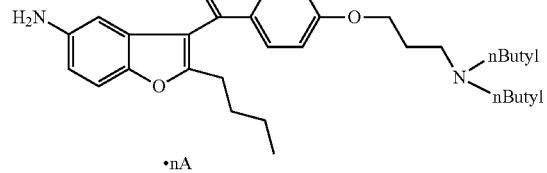

(II)

where
A is a mono- or dibasic acid forming an acid addition salt with the compound of formula (II), and n is 1 if A is dibasic acid, and n is 1 or 2 if A is a monobasic acid, with the proviso that A is different from oxalic acid.

A further aspect is a process for preparation of novel salts of compound of formula (II)

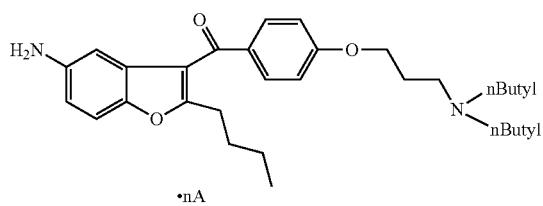

(II)

where

A is a mono- or dibasic acid forming an acid addition salt with the compound of formula (II), and n is 1 if A is dibasic acid, and n is 1 or 2 if A is a monobasic acid, with the proviso that A is different from oxalic acid, in which the nitro group of compound of formula (III)

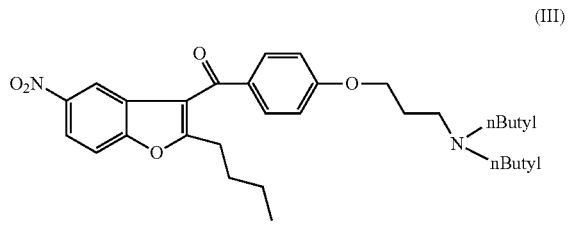

(III)

is hydrogenated in a solvent in the presence of acid A.

A further aspect is the use of a salt of (5-amino-2-butyl-1-benzofuran-3-yl){4-[3-(di-n-butylamino)propoxy]-phenyl}methanone of formula (II)

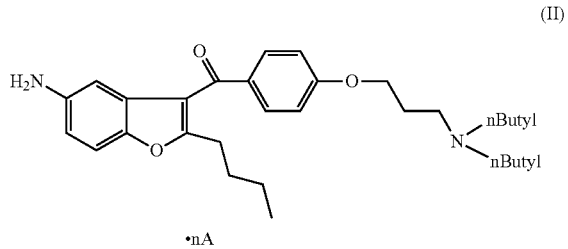

(II)

where

A is a mono- or dibasic acid forming an acid addition salt with the compound of formula (II), and n is 1 if A is dibasic acid, and n is 1 or 2 if A is a monobasic acid, for the preparation of N-[2-n-butyl-3-[4-[3-(di-n-butylamino)-propoxy]-benzoyl]-benzofuran-5-yl]methanesulfonamide (I)

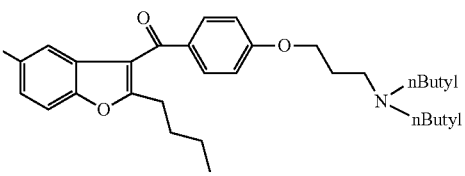

(I)

and pharmaceutical acceptable salts thereof. In this use the said compound of formula (II) is mesylated by reacting it with a mesylating agent in a heterogeneous reaction, if desired in the presence of a phase transfer catalyst.

DETAILED DESCRIPTION OF THE INVENTION

The present invention provides a new method to perform the mesylation reaction starting from the above new salts of compound of formula (II). This method is simple and practical; there is no need to use different amines for binding the acids produced in the mesylation reaction, moreover, using the new salts of compound of formula (II) negligable bis-mesylated product (<0.1%) is formed which makes unnecessary the material consuming purification for the removal of bis-mesylated product. The above salts of compound of formula (II) can be prepared in a simply way by mixing the base of formula (II) with one or two equivalents of desired acid.

The starting amine base of formula (II) is known from EP 0471609. The oxalate salt of compounds of formula (II) is also known from the Example 2 of EP 0471609 which can be applied for the purification of compounds of formula (II). Other salts are not known from the prior art. However, moderate yields and purity can be achieved by the use of the oxalate salt in the invented process (i.e. it is not an advantageous embodiment).

Without binding ourselves to the following theory, we suppose that the heterogeneous character of the reaction plays an important role in the selectivity of the mesylation reaction (selectivity for the preparation of mono-mesylated product). In this process the salt form of the compound of formula (II) is not soluble in the applied inert solvent (which can be a solvent mixture, too), but the base form and the dissociated acid (acid A) is soluble in the applied solvent (where the mesylating compound is also solved). We suppose that after the formation of the mono-mesylated compound a salt formation takes place at the di-N-alkylated amino group (see the "right side" of the molecule) and the formed salt leaves the inert solvent, and it hinders the formation of the di-mesylated product. This theory gives an explanation for the found surprising selectivity for the mono-mesylation.

The phrases "insoluble" or "does not solve" have the general meaning applied in the field of chemistry, i.e. refers to a very poor solubility (less than 0.1 or 0.01% or 0.001 by weight solution can be made from the substance) since a minimal solubility obviously cannot be excluded theoretically. The phrases "soluble" and "can be solved" refers to a much better solubility (more than 0.1, e.g. more than 1% by weight solution can be made from the substance).

The applicable acid can be any inorganic or organic acid which forms an acid addition salt with the compound of general formula (II). Exemplary meanings of acid A are as follows: acetic acid, adipic acid, alginic acid, ascorbic acid, aspartic acid, benzoic acid, benzenesulfonic acid, methansulfonic acid, ethansulfonic acid, boric acid, butyric acid, citric acid, ethanesulfonic acid, fumaric acid, hydrogen chloride, hydrogen bromide, hydrogen iodide, 2-hydroxyethanesulfonic acid, maleic acid, methanesulfonic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt. Moreover, methanesulfonic acid and p-toluenesulfonic acid salts are also practical.

The reaction is carried out typically at temperature of 50-140° C., e.g. 65 to 100° C., typically under atmospheric pressure.

The heterogeneous character of the reaction can be ensured by the proper selection of the solvent applied in the reaction. Such solvent should be applied in which the salt of (5-amino-2-butyl-1-benzofuran-3-yl){4-[3-(di-n-butylamino)propoxy]phenyl}-methanone of formula (II) is not soluble but the base form of it and the acid A are soluble. Otherwise the solvent should be inert, i.e. it must not react with any reagent applied in the process.

In one embodiment the solvent is selected from the group of aromatic compounds, halogenated aromatic compounds, halogenated alkanes or cycloalkanes, ethers and ketones and any mixtures thereof. Typically, the solvent is selected from the group of toluene, xylene, chlorobenzene, anisole, dichloroethane, heptane, 2-methyl cyclohexane, dibutylether, methylethyl ketone and any mixtures thereof.

In the process a mesylating reagent should be applied. It can be any reagent which can be used for inserting of $CH_3SO_2$— group into the free amino group of compound of general formula (II) [see the "left side" of general formula (II)]. It is advantageous to use methanesulfonic anhydride or methanesulfonyl halogenide, e.g. methanesulfonyl chloride.

With respect to the heterogeneous character of the invented process, it is advantageous to apply a phase transfer catalyst. This phrase is obvious for a skilled person and embraces such substances which enables the dissolution of the base form compound of formula (II) into the applied inert solvent. The phase transfer catalyst is typically a quaternary ammonium salt, e.g. quaternary ammonium chloride.

The salts of compound of formula (II) can be prepared by known procedures. Typically the (5-amino-2-butyl-1-benzofuran-3-yl){4-[3-(dibutylamino)propoxy]phenyl}-methanon of formula (II) is reacted with 1 or 2 equivalents of acid A (which is typically hydrogen chloride, hydrogen bromide, methanesulfonic acid, p-toluenesulfonic acid, e.g. hydrogen chloride). The reaction is carried out in a usual inert solvent (or solvent mixture) and the obtained salt is separated (if desired, it can be further purified by known purification methods).

In another embodiment of the invention the salts of compound of formula (II) can be prepared by reducing (hydrogenating) the nitro group of compound of formula (III)

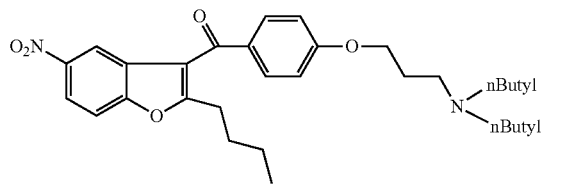

(III)

in presence of 1 or 2 equivalents of acid A (see above). The obtained product can be used in the mesylation step without further purification.

The above reduction is a hydrogenation process which is carried out in a solvent usually applied in hydrogenation methods (typically $C_{1-4}$ alcohols (e.g. methanol and ethanol), ethyl acetate, cyclohexane) in presence of usual catalyst generally used for hydrogenation (e.g. Pd or Pt catalyst, especially for hydrogenation of a nitro group, e.g. Pd/C).

Accordingly, the dronedarone (I) and pharmaceutical acceptable salts thereof can be prepared by a process wherein the compound of formula (III) is hydrogenated in a solvent (or solvent mixture) in the presence of an acid A (see above, which is typically hydrochloric acid, hydrobromic acid or methanesulfonic acid), and after completion of the reaction the catalyst is filtered out, the solvent is removed and the residual salt of formula (II) is reacted in another solvent with a mesylating reagent (as it is discussed above), the obtained salt of dronedarone of formula (I) is separated and, if desired, the base form of dronedarone of formula (I) is deliberated and, if desired, another salt thereof is formed.

EXAMPLES

Example 1

N-[2-n-butyl-3-[4-[3-(di-n-butylamino)propoxy]benzoyl]benzofuran-5-yl]methanesulfonamide (I)

1 g of (5-amino-2-butyl)-1-benzofuran-3-yl)[4-[3'-(di-n-butylamino)propoxy]-phenyl]-methanone dihydrochloride salt and 0.12 g of tetrabutylammonium chloride is added to 10 ml of toluene. It is heated under stirring to 80-90° C. and at this temperature 0.41 g of methanesulfonyl chloride is added in 30 minutes. The mixture is stirred at 80-90° C. for 5 hours. The mixture is cooled to room temperature and 10 ml of ethyl acetate and 10 ml of water are added. The organic layer is separated and the aqueous layer is extracted with 5 ml of ethyl acetate. The combined organic layers are dried on. $Na_2SO_4$ and evaporated.

Yield: 1.07 g (99.5%).

This product is purified by forming its oxalate salt as follows: to the residue 4 ml of methylethyl ketone is added and the mixture heated to 70° C. To this solution 0.22 g of oxalic acid dissolved in 2.5 ml of methylethyl ketone is added at 70° C. After cooling to 20° C. in 6 hours the mixture is stirred at 10° C. for 1 hour and filtered. To the obtained oxalate salt 3.5 ml of water and 5 ml of dichloromethane and 0.59 g of potassium carbonate are added. After stirring for 30 minutes the separated potassium oxalate is filtered and washed with 3 ml of dichloromethane and the solvent is evaporated.

Mass of purified product 0.98 g (92%).

Purity of the obtained title product: 99.8% (HPLC).

HNMR (DMSO): 0.8-0.9 ppm (m, 9H); 1.2-1.5 pp (m, 10H); 1.67 ppm (5', 2H); 1.87 ppm (5', 2H); 2.38 ppm (t, J=7.2 Hz, 4H); 2.57 ppm (m, 2H); 2.81 ppm (t, J=7.5 Hz, 2H); 2.91 ppm (s, 3H); 4.15 ppm (t, J=6.2 Hz, 2H); 7.09 ppm (d, J=8.8 Hz, 2H); 7.24 ppm (dd, J=8.9, 2.2 Hz, 1H); 7.34 ppm (d, J=2.1 Hz; 1H); 7.65 ppm (d, J=8.8 Hz, 1H); 7.81 ppm (d, J=8.8 Hz, 2H)

Example 2

The process according to example 1 is performed with the difference that chlorobenzene is used instead of toluene.

Yield of the product after purification through its oxalate salt according to example 1: 94.6%. Purity (HPLC): 99.7%.

Example 3

The process according to example 1 is performed with the difference that 0.04 g of tetramethyl ammonium chloride is used instead of tetrabutyl ammonium chloride.

Yield of the product after purification through its oxalate salt according to example 1: 95.1%. Purity (HPLC): 99.6%.

Example 4

N-[2-n-butyl-3-[4-[3-(di-n-butylamino)propoxy]benzoyl]benzofuran-5-yl]methanesulfonamide (I)

0.9 g of (5-amino-2-butyl)-1-benzofuran-3-yl)[4-[3-(di-n-butylamino)propoxy]-phenyl]methanone is dissolved in 10 ml of dichloromethane. 0.37 g of methanesulfonic acid is added in 5 minutes and the mixture is stirred for 5 minutes. The solvent is evaporated. To the residual salt mixed with 10 ml of heptane and 0.11 g of triethylbenzyl ammonium chloride is added and the mixture is heated to 80-90° C. At this temperature 0.62 g of methansulfonic anhydride is added in 5 minutes and the mixture is stirred at this temperature for additional 5 hours. After cooling to room temperature 15 ml of ethyl acetate and 1 ml of sodium hydrocarbonate (5%) is added. The organic layer is washed with 5 ml of water and evaporated.

Yield: 0.98 g (94.8%). This product is purified through its oxalate salt according to example 1 (yield: 90.6%). Purity of the obtained title product (HPLC): 99.8%.

Example 5

N-[2-n-butyl-3-[4-[3-(di-n-butylamino)propoxy]benzoyl]benzofuran-5-yl]methanesulfonamide (I)

4.8 g of (5-amino-2-butyl)-1-benzofuran-3-yl)[4-[3-(di-n-butylamino)propoxy]-phenyl]methanone is dissolved in 15 ml of abs. ethanol and 0.9 ml of hydrochloric acid of 37% is added in 10 minutes. The solution is stirred at 50° C. for 30 minutes and completely evaporated in reduced pressure. The residual material: 5.1 g (99%) (5-amino-2-butyl)-1-benzofuran-3-yl)[4-[3-(di-n-butylamino)propoxy]phenyl]-methanone monohydrochloride salt.

To this salt 0.5 g of tetrabutylammonium chloride and 50 ml of toluene are added and heated to 80-90° C. At this temperature 1.9 g of methanesulfonyl chloride is added in 30 minutes. This mixture is stirred at 80-90° C. for 5 hours and cooled to room temperature. 50 ml of ethylacetate and 50 ml of water are added and the phases are separated. The aqueous layer is washed with 25 ml of ethyl acetate. The combined organic layer is dried with $Na_2SO_4$ and evaporated.

Yield: 5.4 g (99%). This product is purified through its oxalate salt according to example 1 (yield: 87%). Purity of the obtained title product (HPLC): 99.7%.

The product is identical with the compound prepared in Example 1.

Example 6

(5-amino-2-butyl-1-benzofuran-3-yl)[4-[3-(di-n-butylamino)propoxy]phenyl]-methanone dihydrochloride (II)

4.8 g of (5-amino-2-butyl)-1-benzofuran-3-yl)[4-[3-(di-n-butylamino)propoxy]-phenyl]methanone is dissolved in 15 ml of abs. ethanol and 1.8 ml of hydrochloric acid of 37% is added in 10 minutes. The solution is stirred at 50° C. for 30 minutes and completely evaporated in reduced pressure. The residual foam solidified cool.

Mp.: 81.5-82.1° C.

Yield: 5.5 g (99%). Purity (HPLC): 99.8%.

1HNMR (DMSO): 7.8 ppm (d, J=8.7 Hz, 2H); 7.78 ppm (d, J=8.93 Hz, 1H); 7.47 ppm (d, J=2.29 Hz, 1H); 7.36 ppm (dd, J=8.81 2.17 Hz, 1H); 7.11 ppm (d, J=8.93 Hz, 2H); 4.21 ppm (t, J=6.07 Hz, 2H); 3.17-3.25 ppm (m, 2H); 3.01-3.09 ppm (m, 4H); 2.80 ppm (t, J=7.75 Hz, 2H); 2.17-2.25 ppm (m, 2H); 1.62-1.71 ppm (m, 6H); 1.33 ppm (sxt, J=7.42 Hz, 4H) 1.22 ppm (sxt, J=7.42 Hz, 2H), 0.91 ppm (t, J=7.32 Hz, 6H); 0.79 ppm (t, J=7.44 Hz, 3H)

Molecular mass: $[M+2H]^{2+}_{measured}$=240.1657 Da; $[M+2H]^{2+}_{calc}$=240.1676 Da.

Example 7

(5-amino-2-butyl)-1-benzofuran-3-yl)[4-[3-(di-n-butylamino)propoxy]phenyl]-methanone dihydrochloride (II)

5.08 g of (2-n-butyl-5-nitro-1-benzofuran-3-yl)[4-(di-n-butylamino)propoxy]-phenyl]methanone (III) is dissolved in 50 ml of ethanol and 0.3 g of Pd/C (10%) is added. Under stirring 1.8 ml of hydrochlorid acid (37%) is added to the mixture and heated to 50° C. and is, set under $H_2$ pressure of 10 bar. After 4 hours reaction time the mixture is cooled down to room temperature, the catalyst is filtered and the solvent is evaporated under reduced pressure.

Yield: 5.5 g (99%). Purity of product (HPLC): 97.6%.

The product is identical with compound prepared in Example 6

Example 8

N-[2-n-butyl-3-[4-[3-(di-n-butylamino)propoxy]benzoyl]benzofuran-5-yl]methanesulfonamide (I)

5.08 g of (2-n-butyl-5-nitro-1-benzofuran-3-yl)[4-(di-n-butylamino)propoxy]-phenyl]methanone (III) is dissolved in 50 ml of ethanol and 0.3 g of Pd/C (10%) and 1.8 ml of hydrochlorid acid (37%) are added. Under stirring the mixture is heated to 50° C. and is set under $H_2$ pressure of 10 bar. After 4 hour reaction time at 50° C. the mixture is cooled down to room temperature, the catalyst is filtered and the solvent is evaporated under reduced pressure. To the residual salt 50 ml of toluene and 4.8 g of tetramethylammonium chloride are added and the mixture is heated to 80-90° C. At this temperature 2.25 g of methansulfonyl chloride is added in 30 minutes and the mixture is stirred at this temperature for 6 hours. After cooling down to 25° C. 60 ml of isopropyl acetate and 25 ml of aq. sodium hydrocarbonate of 5% are added and stirred for 10 minutes. The phases are separated. The organic layer is washed with 10 ml of water. After drying on $Na_2SO_4$ the solvent is evaporated.

Yield: 5.5 g (99.1%). The product is purified by its oxalate salt according to example 1 (yield: 94%). Purity of the obtained title product: 99.7% (HPLC).

The product is identical with compound prepared in example 1.

The invention claimed is:

1. A process for preparing N-[2-n-butyl-3-[4-[3-(di-n-butylamino)-propoxy]-benzoyl]-benzofuran-5-yl]methanesulfonamide (I)

(I)

[chemical structure of formula (I)]

and pharmaceutically acceptable salts thereof, comprising reacting a salt of (5-amino-2-butyl-1-benzofuran-3-yl){4-[3-(di-n-butylamino)propoxy]phenyl}methanone of formula (II)

(II)

[chemical structure of formula (II) with nA]

where

A is a mono- or dibasic acid forming an acid addition salt with the compound of formula (II), and n is 1 if A is dibasic acid, and n is 1 or 2 if A is a monobasic acid, with a mesylating reagent in a heterogeneous reaction, optionally, in the presence of a phase transfer catalyst.

2. The process according to claim 1, wherein the acid A is selected from the group consisting of hydrogen chloride, hydrogen bromide, methanesulfonic acid, p-toluenesulfonic acid and sulphuric acid.

3. The process according to claim 2 wherein the heterogeneous reaction uses a solvent in which the salt of (5-amino-2-butyl-1-benzofuran-3-yl){4-{3-(di-n-butylamino)propoxy]phenyl}-methanone of formula (II) is not soluble and the base form of it and acid A are soluble.

4. The process according to claim 3, wherein the solvent is selected from the group consisting of aromatic compounds, halogenated aromatic compounds, halogenated alkanes or cycloalkanes, ethers and ketones and any mixtures thereof.

5. The process according to claim 4, wherein, the solvent is selected from the group consisting of toluene, xylene, chlorobenzene, anisole, dichloroethane, heptane, 2-methyl cyclohexane, dibutylether, methylethyl ketone and any mixtures thereof.

6. The process according to claim 1, wherein the mesylating agent is methanesulfonic anhydride or methanesulfonyl halogenide.

7. The process according to claim 1, wherein the reaction is carried out in the presence of a phase transfer catalyst.

8. A process for preparing the salt of compound formula (II)

(II)

[chemical structure of formula (II) with nA]

where

A is hydrogen chloride or methanesulfonic acid, forming an acid addition salt with the compound of formula (II), and n is 1 or 2, comprising hydrogenating the nitro group of compound of formula (III)

(III)

[chemical structure of formula (III)]

in a solvent in the presence of acid A.

9. The process according to claim 8, wherein the hydrogenation process is carried out in a solvent in the presence of a Pd or Pt catalyst.

10. The process according to claim 9, wherein the solvent is selected from the group consisting of $C_{1-4}$ alcohols, ethyl acetate and cyclohexane.

11. The process of claim 1, further comprising a process for preparing the salt of compound formula (II) comprising hydrogenating the nitro group of compound of formula (III)

(III)

[chemical structure of formula (III)]

in a solvent in the presence of acid A, with the proviso that A is different from oxalic acid.

12. The process according to claim 11, wherein the acid A is selected from the group consisting of hydrogen chloride, hydrogen bromide, methanesulfonic acid, p-toluenesulfonic acid and sulphuric acid.

13. The process according to claim 11, wherein the hydrogenation process is carried out in a solvent in the presence of a Pd or Pt catalyst.

14. The process according to claim 13, wherein the solvent is selected from the group consisting of $C_{1-4}$ alcohols, ethyl acetate and cyclohexane.

* * * * *